United States Patent [19]
DeLuca et al.

[11] 4,110,446
[45] Aug. 29, 1978

[54] METHOD OF TREATING MILK FEVER IN DAIRY CATTLE WITH 1,25-DIHYDROXYCHOLECALCIFEROL

[75] Inventors: Hector F. DeLuca, Madison; Neal A. Jorgensen, Middleton, both of Wis.

[73] Assignee: Wisconsin Alumni Research Foundation, Madison, Wis.

[21] Appl. No.: 815,587

[22] Filed: Jul. 14, 1977

[51] Int. Cl.² ............................................. A61K 31/59
[52] U.S. Cl. .................................................... 424/236
[58] Field of Search ......................................... 424/236

[56] References Cited
PUBLICATIONS

Pechet et al.–Chem. Abst., vol. 81 (1974), p. 114,855k.

*Primary Examiner*—Sam Rosen
*Attorney, Agent, or Firm*—Howard W. Bremer

[57] ABSTRACT

A method of treatment and prophylaxsis for milk fever in dairy cattle which comprises administering 1,25-dihydroxycholecalciferol to the cattle.

6 Claims, No Drawings

METHOD OF TREATING MILK FEVER IN DAIRY CATTLE WITH 1,25-DIHYDROXYCHOLECALCIFEROL

The invention described herein was made in the course of work under a grant or award from the Department of Health, Education, and Welfare.

This invention relates to a method of treatment and prophylaxsis for milk fever disease in dairy cattle using 1,25-dihydroxycholecalciferol.

Milk fever (parturient paresis) is a metabolic disease of dairy cows in which the cows fail to absorb or mobilize enough calcium at the time of parturition to provide for the production of milk. The disease is manifested by a decrease in plasma calcium, usually between six to thirty hours after parturition, to a value so low as to induce tetany with resultant immobilization of the cow. There is also generally an accompanying decrease in the blood phosphate level. As an example, the plasma calcium level in a cow prior to calving is about 10 mg./100 ml. (or 10 mg. percent). Following parturition this level will normally dip to about 7–8 mg. percent but will then rise in a reasonable time to the more normal 10 mg. percent range. In a cow afflicted with milk fever, however, after parturition the plasma calcium may dip more drastically, such as into the 5 mg. percent range, and it is recognized that at such plasma calcium levels the cow will go into tetany. Such low plasma calcium levels are not necessary in all cases to induce milk fever disease and the disease is experienced at substantially higher calcium levels depending upon the individual animal involved. If treatment for such condition is not however, immediate and successful there is a real danger that the cow may die or be afflicted with a lasting paralysis, or at the very least that its milk production will be substantially decreased. (See "Milk Fever Causes, Methods of Treatment and Prevention," S. H. Morrison, Vol. 1, No. 2, a publication of Borden Chemical Company and J. M. Payne, Brit. Vet. Assn. "Recent Advances in Our Knowledge of Milk Fever," presented at 87th Annual Congress of the Association, Sept. 6, 1964.)

The incidence of milk fever disease has been estimated to be in the range from about 3.5–5% of the world's dairy cows. In individual herds, however, the incidence may be as high as 60–70%. It appears that the incidence of the disease is highest among high milk producing cows during the third and later lactation periods although at times it has been observed in the second lactation period. In any event, once a cow has had milk fever there is an 80–90% probability that she will again be so afflicted after her next parturition.

Prior to the present invention various methods had been suggested for the treatment of milk fever. For example, feeding of a low calcium diet or feeding a high phosphate in a grain ration, which is tantamount to a low calcium diet, has been suggested as a preventative for the disease. Since, however, it is necessary to feed cattle a high calcium diet during their non-lactating periods to replenish the calcium stores depleted by previous milking such treatment is not a very practical solution for milk fever problem. Other methods of treatment suggested include air inflation of the udder — a treatment not used because of the danger of mastitis and other infection — and acidification of silage which alleviated the disease. This latter method is impractical because of problems engendered by the acid intake.

Currently, the most widely used treatment for milk fever is the administration of vitamin D in massive dosage. For example, in one method the cow is fed 20 million units per day of vitamin D for three to seven days before calving while in another method 10 million units of vitamin D is injected intramuscularly before calving. Although these methods are of value they are associated with potentially high risk and other disadvantages. With administration of such large dosages of vitamin D there is a real danger of vitamin D toxicity and, as a consequence, death of the cow or damage through abnormal calcification of the soft tissues such as the kidney, aorta, etc. Even if the animal survives without damage the milk produced would not be fit for human or calf consumption for some time because of the high content of vitamin D in the milk.

Other methods which have been suggested for combatting milk fever disease utilize the administration of 25-hydroxycholecalciferol (U.S. Pat. No. 3,646,203, issued Feb. 29, 1972) and 1α-hydroxycholecalciferol (U.S. Pat. No. 3,879,548).

It has now been found that 1α,25-dihydroxycholecalciferol (1,25-DHCC) can be used in the treatment and prevention of milk fever in dairy cattle and that in such use it is more effective than vitamin D, 25-hydroxycholecalciferol, and 1α-hydroxycholecalciferol. When administered to the cows at least about 24 hours prior to calving 1,25-DHCC has been found to prevent the fall in serum calcium and phosphorous characteristically found in cows during the critical period of 24 hours prior to and 48 hours after calving. (1,25-DHCC is a derivative of vitamin $D_3$ and is more fully described in U.S. Pat. No. 3,697,559, issued Oct. 10, 1972. Method for preparing this compound are set forth in Semmler et al, Tetrahedron Letters No. 40, pp. 4147–4150, 1972, and in U.S. Pat. No. 4,022,768, issued May 10, 1977.)

In general dosages of 1,25-DHCC in the range from about 200–400 µg are effective in preventing milk fever when administered from about 24–72 hours before calving occurs. If more than 5 days elapses from the time of administering the first dose and calving has not occurred an additional dose is generally given. The dose is not critical and can be varied depending at least in part on the size of the animal. In any event, 1,25-DHCC should be administered in amounts sufficient to accomplish the desired treatment or prophylaxsis. The use of more than sufficient 1,25-DHCC to accomplish the ends sought should be avoided as an economically unsound practice.

It will be evident that inasmuch as hypocalcemia is a characteristic of such disorders as milk fever, 1,25-DHCC can also be a treatment of choice for other disorders involving hypocalcemia or for a hypocalcemic condition per se. Also, the 1,25-DHCC can be administered in conjunction with calcium (calcium gluconate), the latter material being fairly commonly used in hypocalcemic situations and particularly where a "downer cow" syndrome is experienced.

Effective and practical administration of 1,25-DHCC can be accomplished by injection of the compound intravenously, intramuscularly or subcutaneously, while dissolved in a suitable vehicle such as an innocuous oil or propylene glycol. Alternatively, the 1,25-DHCC can be compounded with other materials to form a bolus or can be encapsulated so that it lends itself to oral administration.

The rapid response of cows to the administration of 1,25-DHCC, as measured by elevated serum calcium and phosphorous levels, is shown in table below. 5 ml of a solution of 1,25-DHCC in corn oil at a concentration of 80 μg/ml was given to the animals. Measurements shown were the average values (mg/100 ml) of two cows.

Table 1

| Serum | Hours post-injection | | | | |
|---|---|---|---|---|---|
| | 0 | 12 | 24 | 36 | 48 |
| Calcium | 9.7 | 10.6 | 11.8 | 12.1 | 11.7 |
| Phosphorus | 5.2 | 5.1 | 6.1 | 6.7 | 7.2 |

The following example is intended to be illustrative only of the invention and not limiting of the appended claims.

EXAMPLE

1α,25-Dihydroxycholecalciferol (1,25-DHCC), synthesized according to the procedure of Semmler et al, supra, was dissolved at a concentration of 80 μg/ml in corn oil. Five ml of this solution was given intramuscularly at least five days prior to predicted calving, to six randomly selected cows (third parity or more), with re-injections every 5 days until calving. Injections were given in the hamstring muscle 250 cm below the pin bone. Another six cows from the same age group were given no treatment and were considered controls for the experiment. All cows received a diet which provided adequate energy, protein and vitamins according to the National Research Council (NRC), >100 g calcium and <45 g phosphorus daily. Blood samples were takend from each cow in both the treated and untreated groups each day beginning at the times indicated in the Tables below, pre-, during and post-calving for calcium and phosphorus analysis.

Results obtained are presented in the following Tables.

Table 2

Serum calcium (mg/100 ml) levels of untreated (untrt) and cows treated (trt) with 1,25-DHCC

| Animal no.[a] | Lactation no. | Time of injections (days pre-partum) | Initial Ca level[b] | Sampling time (hours) | | | | | | | | |
|---|---|---|---|---|---|---|---|---|---|---|---|---|
| | | | | Pre-partum | | | | Calving | Post-Partum | | | |
| | | | | 96 | 72 | 48 | 24 | 0 | 12 | 24 | 48 | 72 |
| Treated cows | | | | | | | | | | | | |
| 1940H | 5 | 6,1 | 8.5 | 8.4 | 7.3 | 9.6 | 9.5 | 7.8 | 8.6 | 8.5 | 8.3 | 7.9 |
| 1809H | 6 | 1 | 10.0 | | 10.8 | 9.9 | 10.0 | 10.4 | 11.3 | 10.3 | 9.0 | |
| 1998H | 4 | 12,7,2 | 8.4 | 9.9 | 9.4 | 9.9 | 12.9 | 11.0 | 11.9 | 9.0 | 10.2 | 10.4 |
| 1892H | 5 | 6,1 | 11.1 | 12.6 | 10.9 | 10.4 | 11.2 | 10.6 | 11.5 | 10.6 | 11.9 | 10.6 |
| 1917H | 5 | 6,0 | 9.8 | 10.8 | 10.6 | 9.8 | 7.7 | 6.6 | 8.6 | 10.4 | 11.1 | 10.3 |
| 2013H | 4 | 8,3 | 9.6 | 11.4 | 11.2 | 11.5 | 12.0 | 9.8 | 10.0 | 10.0 | 9.5 | 9.6 |
| Average(trt) | 4.8 | | 9.6 | 10.6 | 9.9 | 10.3 | 10.5 | 9.3 | 10.2 | 10.0 | 10.2 | 9.6 |
| Untreated cows | | | | | | | | | | | | |
| 2029H | 3 | | 9.3 | 8.7 | 9.0 | 9.5 | 9.6 | 8.2 | 6.1 | 7.1 | 8.7 | |
| 1989H | 4 | | 10.1 | 10.0 | 9.7 | 9.5 | 9.3 | 9.3 | 7.0 | 8.4 | 10.6 | 9.9 |
| 1929H | 5 | | 9.9 | 12.0 | 10.0 | 10.0 | 8.1 | 7.1 | 6.1[c] | 9.0 | 6.5 | 7.0 |
| 2013H | 3 | | 8.8 | 9.4 | 9.1 | 10.2 | 8.3 | 7.5 | 8.3 | 7.8 | 8.8 | 9.5 |
| 1985H | 4 | | 9.0 | | 9.4 | 9.0 | 9.2 | 8.6 | 4.0[c] | 6.9 | 8.6 | 8.7 |
| 391S | 3 | | 8.9 | 9.0 | 8.9 | 8.8 | 9.4 | 8.6 | 7.6 | 6.4 | 7.0 | 9.4 |
| Average (untrt) | 3.7 | | 9.3 | 9.8 | 9.4 | 9.5 | 9.0 | 8.2 | 6.5 | 7.6 | 8.4 | 8.9 |
| Difference (avg$_{trt}$−avg$_{untrt}$) | | | 0.3 | 0.6 | 0.5 | 0.8 | 1.5 | 1.1 | 3.7 | 2.4 | 1.8 | 0.7 |
| Significance[d] | | | — | — | — | — | * | — | *** | *** | ** | — |
| Standard error (treated) | | | 0.41 | 0.71 | 0.71 | 0.29 | 0.77 | 0.70 | 0.57 | 0.43 | 0.51 | 0.42 |
| Standard error (untreated) | | | 0.22 | 0.59 | 0.18 | 0.22 | 0.25 | 0.32 | 0.61 | 0.40 | 0.60 | 0.51 |

[a]H = Holstein; S = Brown Swiss.
[b]Sample taken 14 days before predicted calving date.
[c]Down with parturient paresis.
[d]*P <.10, P <.05, *P <.01.

Table 3

Serum phosphorus (mg/100 ml) levels of untreated (untrt) and cows treated (trt) with 1,25-DHCC

| Animal no.[a] | Lactation no. | Time of injections (days pre-partum) | Initial P level[b] | Sampling time (hours) | | | | | | | | |
|---|---|---|---|---|---|---|---|---|---|---|---|---|
| | | | | Pre-partum | | | | Calving | Post-partum | | | |
| | | | | 96 | 72 | 48 | 24 | 0 | 12 | 24 | 48 | 72 |
| Treated cows | | | | | | | | | | | | |
| 1940H | 5 | 6,1 | 6.1 | 9.8 | 10.1 | 9.8 | 9.7 | 8.6 | 9.4 | 8.5 | 9.4 | 7.3 |
| 1809H | 6 | 1 | 5.1 | | | 6.3 | 5.5 | 5.5 | 6.1 | 6.1 | 7.6 | 3.6 |
| 1998H | 4 | 12,7,2 | 5.1 | 11.1 | 13.0 | 10.9 | 11.2 | 10.6 | 10.4 | 10.9 | 9.5 | 8.1 |
| 1892H | 5 | 6,1 | 4.8 | 7.7 | 8.3 | 7.9 | 6.7 | 6.8 | 8.3 | 9.5 | 9.3 | 9.0 |
| 1917H | 5 | 6,0 | 6.4 | 9.5 | 10.3 | 8.8 | 9.1 | 7.0 | 7.9 | 9.1 | 9.5 | 8.8 |
| 2013H | 4 | 8,3 | 3.8 | 10.8 | 8.7 | 8.4 | 9.5 | 9.5 | 9.0 | 10.6 | 11.6 | 10.9 |
| Average(trt) | 4.8 | | 5.2 | 9.8 | 10.0 | 8.7 | 8.6 | 8.0 | 8.5 | 9.1 | 9.5 | 8.0 |
| Untreated cows | | | | | | | | | | | | |
| 2029H | 3 | | 3.9 | 7.3 | 7.1 | 6.5 | 4.9 | 3.5 | 5.2 | 5.5 | 4.4 | |
| 1989H | 4 | | 4.5 | 4.6 | 5.9 | 5.2 | 4.5 | 2.3 | 1.8 | 5.5 | 6.4 | 7.1 |
| 1929H | 5 | | 5.9 | 4.5 | 6.0 | 6.0 | 3.6 | 1.9 | 2.1[c] | 3.5 | 2.7 | 4.1 |
| 2013H | 3 | | 5.5 | 5.8 | 4.5 | 5.3 | 4.2 | 3.8 | 4.7 | 3.8 | 5.3 | 4.4 |
| 1985H | 4 | | 6.2 | | 5.9 | 6.2 | 5.9 | 7.6 | 4.2[c] | 6.8 | 9.5 | 11.4 |
| 391S | 3 | | 3.5 | 5.2 | 5.7 | 6.1 | 5.4 | 6.2 | 4.9 | 4.7 | 4.3 | 5.3 |
| Average(untrt) | 3.7 | | 4.9 | 5.5 | 5.9 | 5.9 | 4.8 | 4.2 | 3.8 | 5.0 | 5.4 | 6.5 |
| Difference (avg$_{trt}$−avg$_{untrt}$) | | | 0.3 | 4.3 | 4.1 | 2.8 | 3.8 | 3.8 | 4.7 | 4.1 | 4.1 | 1.5 |
| Significance[d] | | | — | *** | *** | *** | *** | *** | *** | *** | *** | — |
| Standard error (treated) | | | 0.38 | 0.60 | 0.83 | 0.65 | 0.86 | 0.78 | 0.60 | 0.71 | 0.52 | 1.00 |

Table 3-continued

| | | | | Serum phosphorus (mg/100 ml) levels of untreated (untrt) and cows treated (trt) with 1,25-DHCC | | | | | | | | |
|---|---|---|---|---|---|---|---|---|---|---|---|---|
| | | | | Sampling time (hours) | | | | | | | | |
| Animal | Lactation | Time of injections | Initial P | Pre-partum | | | | Calving | Post-partum | | | |
| no.[a] | no. | (days pre-partum) | level[b] | 96 | 72 | 48 | 24 | 0 | 12 | 24 | 48 | 72 |
| Standard error (untreated) | | | 0.45 | 0.51 | 0.34 | 0.21 | 0.34 | 0.91 | 0.61 | 0.50 | 0.95 | 1.34 |

[a,b,c,d]See footnotes in Table 2

It is evident from the data in the foregoing Tables 2 and 3 that 1,25-DHCC demonstrates a marked ability to prevent the fall in serum calcium and phosphorus levels of aged cows during and post-calving and is particularly effective in maintaining blood calcium and phosphorous values during the critical period from about 24 hours pre- to 48 hours post-calving thereby preventing parturient paresis. The incidence of parturient paresis was zero in the treated cow group and 33% (2 out of 6) in the untreated group.

It is also evident from a comparison of the data in the foregoing Tables 2 and 3 with the data presented in U.S. Pat. Nos. 3,646,203 and 3,879,548 relating to the treatment of milk fever with, respectively, 25-hydroxycholecalciferol and 1α-hydroxycholecalciferol, that the benefits afforded by the 1,25-DHCC treatment of this invention are eminently superior.

The rapid response to the treatment as shown in Table 1 strongly suggests the use of 1,25-DHCC in conjunction with intravenous calcium (calcium gluconate) administration to prevent tetany in a cow with milk fever and the "downer cow" syndrome.

Having thus described the invention what is claimed is:

1. The method of treatment and prophylaxsis for milk fever disease in cattle which comprises administering to the cattle 1,25-dihydroxycholecalciferol in an amount sufficient to induce said treatment and prophylaxsis.

2. The method of claim 1 wherein the 1,25-dihydroxycholecalciferol is administered in conjunction with calcium.

3. The method of claim 1 wherein the treatment comprises administering from about 200 to 400 μg of 1,25-dihydroxycholecalciferol to each cow at least one day prior to calving.

4. The method of claim 1 wherein the treatment is by injection.

5. The method of claim 1 wherein the treatment is oral.

6. The method of treatment and prophylaxis for downer cow syndrome in cattle which comprises administering to the cattle 1,25-dihydroxycholecalciferol in an amount sufficient to induce said treatment and prophylaxis.

* * * * *